United States Patent [19]
Duffy et al.

[11] Patent Number: 5,101,830
[45] Date of Patent: Apr. 7, 1992

[54] BLOOD PRESSURE CUFF AND TO A METHOD OF MAKING THE SAME

[75] Inventors: Karen M. Duffy, Milford; Michael Williams, Coventry, both of Conn.

[73] Assignee: CAS Medical Systems, Inc., Branford, Conn.

[21] Appl. No.: 625,804

[22] Filed: Dec. 11, 1990

[51] Int. Cl.$^5$ ............................................. A61B 5/022
[52] U.S. Cl. ................................................... 128/686
[58] Field of Search ............... 128/677, 686, DIG. 20; 606/202

[56] References Cited
U.S. PATENT DOCUMENTS

| | | | |
|---|---|---|---|
| 3,654,931 | 4/1972 | Hazlewood | 606/202 |
| 4,033,337 | 7/1977 | Raczkowski | 128/686 |
| 4,838,276 | 6/1989 | Nagai et al. | 128/686 |

*Primary Examiner*—William E. Kamm
*Assistant Examiner*—Kevin Pontius
*Attorney, Agent, or Firm*—William W. Jones

[57] ABSTRACT

A polyurethane coated nylon sheet is folded medially to form the pressure cuff. The urethane coated surface forms the inner surface of the inflation chamber of the cuff. A hook and loop fastener assembly for securing the cuff about the patient's limb is secured to the cuff. The hook and loop sheets are both provided with fusable polymer back coatings. The hook and loop sheets are fused to the polyurethane coated surfaces on the cuff. The hooks and loops are accessible on opposite sides of the cuff. An inflation fitting is also fused to the interior of the pressure chamber and projects through an opening in the cuff.

8 Claims, 1 Drawing Sheet

BLOOD PRESSURE CUFF AND TO A METHOD OF MAKING THE SAME

This invention relates to an improved blood pressure cuff and to a method of making the same.

Blood pressure cuffs frequently use a hook and loop fastener mechanism, such as that sold under the trademark "Velcro" to secure the cuff about the limb of the patient whose blood pressure is being taken. In fabric style cuffs the hook and loop portions of the fastener mechanism are presently being secured to the cuff by stitching hook and loop pads to the cuff about the edges of the pads. This mode of attachment of the fastener components to the cuff is not desirable because it is time consuming to produce and more costly since the stitches must necessarily be placed in the cuff with specialized equipment.

This invention relates to an improved blood pressure cuff which has its hook and loop fastener components bonded to the cuff by means of a heat fusable polymeric coating, or the like. In the cuff of this invention, stitches are not used to secure the fastener components to the cuff. The cuff is made from a fabric tube, such as nylon which is folded from a single sheet preform about a mid axial line to form the tube. The surface of the preform sheet which is brought into face-to-face contact with itself when the tube is formed is coated with a layer of a polymer such as polyurethane which renders the fabric impermeable to air, and which provides a heat activated fusable layer on the interior of the tube. The edges of the tube can thus be fused together to form the inflatable bladder in the cuff. The hook and loop components are each provided with polymer coated backings which can be heat fused to polymer coated surfaces on the preform. Die cut openings are made in the sheet preform at appropriate locations. One of the openings is closed with a polymer coated patch. The patch is larger than said one opening and the polymer surface of the patch is juxtaposed to the polymer surface of the sheet preform, whereupon the patch is fused to the preform. The opening is thus sealed with the patch with the polymer coated surface of the patch being accessible through the opening. The loop component is then secured to the preform by placing the polymer coated surface of the loop component on the polymer coated surface of the patch. The juxtaposed polymer coated surfaces are then fused together by application of heat. The sheet is then folded as noted above, and the edges are appropriately sealed to form the inflation chamber. Folding the sheet preform brings the unclosed die cut opening over, and in registry with, the polymer coated surface of the opposite side of the preform. The hook component is then placed in the opening with its polymer backing surface facing the polymer coated surface of the preform, and fused to the latter through the opening. Both fastener components are thus fused to the folded preform, but there are no exposed polymer coated surfaces of the preform remaining exposed from the exterior of the cuff. An inflation hose fitting can also be secured to the preform in a similar manner. The fitting, or in some cases, fittings, are formed from a like polymer, such as polyurethane, and have radial flanges that abut the polyurethane coating on the sheet preform. A small hole is cut in the preform and the fitting is properly positioned therein, whereupon the flange is fused to the polyurethane coating on the preform.

It is, therefore, an object of this invention to provide an improved blood pressure cuff which employs a hook and loop fastener assembly to secure the cuff about a patient's limb.

It is a further object of this invention to provide an improved blood pressure cuff of the character described which does not employ stitching.

It is another object of this invention to provide an improved blood pressure cuff of the character described wherein the hook and loop fastener components are provided with polymer coated backing surfaces, and are fused to polymer coated surfaces on the cuff.

It is an additional object of this invention to provide an improved blood pressure cuff of the character described which is devoid of exposed polymer coated surfaces.

These and other objects and advantages of the invention will become more readily apparent to those skilled in the art from the following detailed description of a preferred embodiment of the invention, when taken in conjunction with the accompanying drawings, in which.

Figure 1:
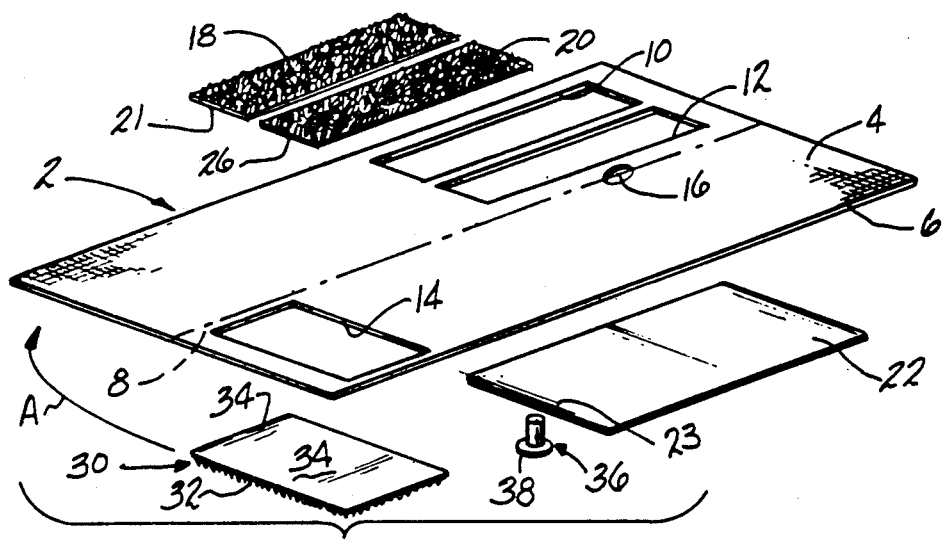
FIG. 1 is an exploded view of the blood pressure cuff of this invention in the preform stage.
Figure 2:
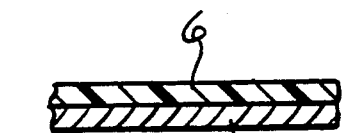
FIG. 2 is a cross sectional view of the coated fabric used to form certain parts of the cuff of FIG. 1.

Referring to FIGS. 1 and 2, there is shown a preferred embodiment of a blood pressure cuff formed in accordance with this invention. The cuff is formed from a sheet preform 2 which is shown in cross section in FIG. 2. The sheet 2 has a fabric component 4 preferably formed from nylon, and a polymeric coating 6 on one side of the fabric component 4 which coating is preferably polyurethane. As seen in FIG. 1, the nylon fabric 4 is face up, and the polyurethane coated surface 6 is face down. The sheet 2 is rectangular, and has a medial fold line 8 (shown in phantom) which traverses the longer dimension of the sheet 2. The fold line 8 divides the sheet 2 into two opposite halves. Openings 10 and 12 are die cut in one half of the sheet, and an opening 14 is die cut in the other half of the sheet 2 diagonally opposite the openings 10 and 12. A small opening 16 is cut in the sheet 2 at the fold line 8 in the general area of the openings 10 and 12.

Two loop fastener components 18 and 20 are adhered to a nylon/urethane coated patch 22. As viewed in FIG. 1, the patch 22 has its polyurethane coated surface 23 facing upward so as to face the polyurethane coated surface 6 of the sheet preform 2. The patch 22 is adhered to the sheet preform 2 to close the openings 10 and 12 by bringing the polyurethane coated surface 23 on the patch 22 against the polyurethane coated surface 6 on the preform 2, and then heat fusing the patch 22 to the preform 2. The loop components 18 and 20 are each provided with fusable polymer coated backing surfaces 21 and 26 respectively. These surfaces 21 and 26 are brought into abutting contact with the coated surface 23 on the patch 22, and the components 18 and 20 are then fused to the patch 22. The loop components 18 and 20 are thus secured in place for use on the cuff. An inflation hose fitting 36 formed from polyurethane, and having a radial flange 38 is inserted from the coated side 6 of the sheet 2 so as to project through the opening 16, with the flange 38 abutting the side 6 of the sheet 2. The flange 38 is then fused to the side 6 of the sheet 2. When the preform 2 is folded about the fold line 8, the opening 14 is brought into registry with the polyurethane coated surface 6 of the preform 2. The hook component 30, as seen in FIG. 1, has its hook surface 32 facing downwardly, and has its polymer coated surface 34 facing upwardly, toward the polymer coated surface 6 of the preform 2. In assembling the cuff, the hook component 30 has its coated surface 34 pressed against the preform coated surface 6 through the opening 14, and is then heat fused to the preform surface 6. The hook component 30 is thus secured to the cuff, opposite the loop components 18 and 20. The dimensions of the hook component 30 equal, or are slightly smaller than the those of the opening 14 so that the hook component 30 covers the opening 14.

Figure 3:
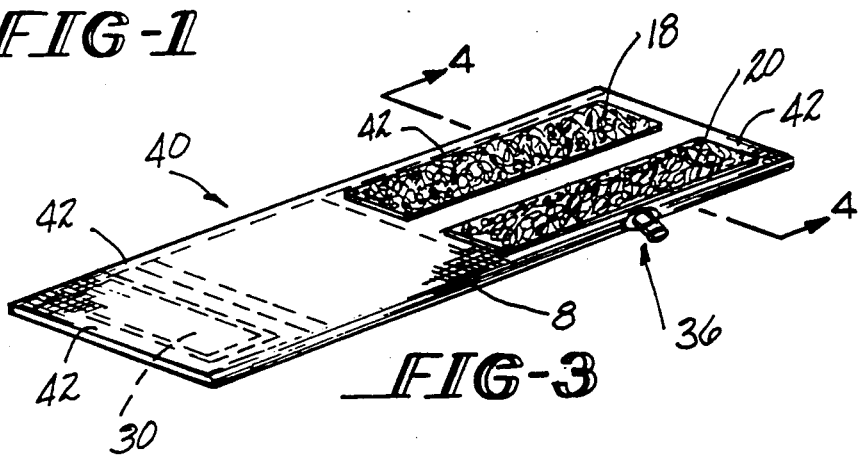
FIG. 3 is a perspective view of the cuff after the preform of FIG. 1 has been folded and sealed.
Figure 4:
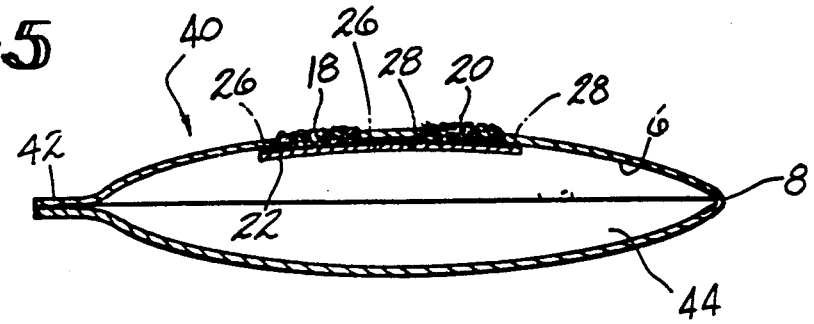
FIG. 4 is a sectional view taken along line 4—4 of FIG. 3.

Referring to FIGS. 3 and 4, details of the assembled cuff 40 are shown. It will be noted that the loop components 18 and 20 are accessible on one side of the cuff 40, and the hook component 30 is accessible on the opposite side of the other end of the cuff 40. The edges of the cuff 40, at 42, are sealed together to form an internal inflatable chamber 44, with which chamber the fitting 36 communicates. It will be noted that the fold 8 forms one edge of the chamber 44. FIG. 4 also clearly illustrates the manner in which the patch 22 is sealed to the polyurethane coated surface of the cuff 40.

Figure 5:
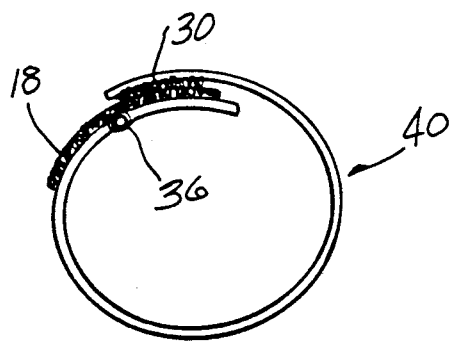
FIG. 5 is an end view of the cuff after the latter has been secured in a limb-encircling configuration.

FIG. 5 shows the cuff 40 looped about itself for affixation to a patient's limb, wherein the hook component 30 is brought into contact with the loop components 18 and 20.

It will be readily appreciated that the cuff of this invention is of simple construction, easy to assemble and reliable. The inflation chamber is not compromised by the securement of the fastening components to the cuff. The particular polymers used for the coatings are selected for their ability to seal the cuff against air permeability, and should be heat fusable.

Since many changes and variations of the disclosed embodiment of the invention may be made without departing from the inventive concept, it is not intended to limit the invention otherwise than as required by the appended claims.

What is claimed is:

1. An inflatable blood pressure cuff formed from a woven fabric sheet having one surface thereof coated with a fusable polymer to render the fabric impermeable to air, said coated sheet surface forming the interior of the cuff, and said sheet being folded upon itself to bring said coated sheet surface into contact with itself, said cuff including an inflatable chamber bounded by edges of said coated sheet surface which edges are fused together; said chamber having one side thereof formed with a cut window therein; and a first hook and loop fastener component mounted on a path of fusable polymer-coated woven fabric by being bonded to a coated surface, said patch being disposed in said chamber with said fastener component protruding through said window, and said patch having edges of said coated surface thereof fused to said coated sheet surface to seal said window thereby sealing the edges of said window against passage of air; said cuff including a second fastener component thereon.

2. The blood pressure cuff of claim 1 wherein said fusable polymer is polyurethane.

3. The blood pressure cuff of claim 2 further comprising a polyurethane inflation fitting having a basal flange fused to said coated surface of said sheet in said chamber, said fitting having a tubular portion thereof projecting through an opening in a side of said chamber to access said chamber to an inflation device.

4. The blood pressure cuff of claim 3 wherein said inflation fitting is disposed on a fold line forming one edge of the cuff.

5. The blood pressure cuff of claim 1 further comprising a second hook and loop fastener component complementary to said first component, said second component being bonded to said coated surface of said sheet and accessible from the exterior of the cuff for securement to said first component.

6. A method for forming an inflatable blood pressure cuff from a fabric material having one surface thereof coated with a fusable polymer operable to render the fabric material impermeable to air, said method comprising the steps of:
 a) providing a preform sheet of said material;
 b) cutting a first window in said preform sheet;
 c) providing a patch of said material;
 d) positioning said patch over said window with the coated surfaces of said preform sheet and said patch in face-to-face contact with each other, and fusing said coated surfaces together to close and seal said window;
 e) providing a first hook and loop fastener component with a backing surface thereof coated with said fusable polymer and bonding said first fastener component to said patch through said window by fusing said backing surface to the coated surface of said patch; and
 f) folding said preform sheet about a mid line to bring the coated surface on one half thereof into face-to-face contact with the coated surface on the other half thereof, and fusing edges of the coated surface of said halves together to form an internal air tight inflatable chamber for the cuff.

7. The method of claim 6 comprising the further steps of cutting a second window in said preform sheet to expose a portion of said coated surface of said preform sheet after said folding step; providing a second hook and loop fastener component complementary to said first component, said second component having a backing surface thereof coated with said fusable polymer; and bonding said second component to said folded preform sheet by fusing said second component backing surface to said portion of said coated surface of said preform through said second window.

8. The method of claim 6 comprising the further steps of cutting an opening in said preform sheet at said mid line thereof; providing a tubular fitting having a basal flange and formed from the fusable polymer; positioning the fitting in said opening with its flange abutting the coated surface of the preform sheet; and fusing the flange to the coated surface of the preform sheet to form a sealed inflation fitting communicating with the chamber in the cuff.

* * * * *